(12) United States Patent
Reddy et al.

(10) Patent No.: US 7,823,591 B2
(45) Date of Patent: Nov. 2, 2010

(54) FEMALE BARRIER CONTRACEPTIVE WITH VACUUM ANCHORING

(76) Inventors: Alla V. K. Reddy, 9 Webster Ct., Plainsboro, NJ (US) 08536; Ravikumar Reddy Alla, 9 Webster Ct., Plainsboro, NJ (US) 08536; Madhusudhan Reddy Alla, 9 Webster Ct., Plainsboro, NJ (US) 08536; Raghunatha Reddy Alla, 9 Webster Ct., Plainsboro, NJ (US) 08536

( * ) Notice: Subject to any disclaimer, the term of this patent is extended or adjusted under 35 U.S.C. 154(b) by 1206 days.

(21) Appl. No.: 11/389,418

(22) Filed: Mar. 24, 2006

(65) Prior Publication Data

US 2006/0231104 A1 Oct. 19, 2006

Related U.S. Application Data

(60) Provisional application No. 60/664,741, filed on Mar. 24, 2005, provisional application No. 60/676,887, filed on May 2, 2005, provisional application No. 60/678,826, filed on May 6, 2005, provisional application No. 60/700,853, filed on Jul. 21, 2005, provisional application No. 60/705,269, filed on Aug. 4, 2005.

(51) Int. Cl.
*A61F 6/06* (2006.01)
*A61F 5/44* (2006.01)
*A61M 1/00* (2006.01)

(52) U.S. Cl. .................. 128/830; 128/834; 128/835; 128/917; 128/918; 604/327; 604/328; 604/330

(58) Field of Classification Search ............... 128/830, 128/834, 835, 842, 844, 917–918; 604/327, 604/330, 347–353

See application file for complete search history.

(56) References Cited

U.S. PATENT DOCUMENTS

| 3,536,066 | A | * | 10/1970 | Ludwig | 128/830 |
|---|---|---|---|---|---|
| 4,735,621 | A | | 4/1988 | Hessel | |
| 4,840,624 | A | | 6/1989 | Lee | |
| 4,867,176 | A | * | 9/1989 | Lash | 128/830 |
| 4,945,923 | A | | 8/1990 | Evans et al. | |
| 4,993,431 | A | | 2/1991 | Reddy | |
| 4,993,433 | A | | 2/1991 | Reddy | |
| 5,325,871 | A | * | 7/1994 | Reddy | 128/830 |
| 5,515,862 | A | | 5/1996 | Artsi et al. | |
| 5,596,997 | A | | 1/1997 | Abadi | |
| 5,992,415 | A | | 11/1999 | Alla et al. | |
| 6,000,398 | A | * | 12/1999 | Alla et al. | 128/844 |
| 6,035,853 | A | * | 3/2000 | Alla et al. | 128/830 |
| 6,223,747 | B1 | | 5/2001 | Rudge et al. | |
| 6,341,607 | B1 | | 1/2002 | Couvreur | |

(Continued)

FOREIGN PATENT DOCUMENTS

FR 2 673 101 8/1992

(Continued)

*Primary Examiner*—Patricia M Bianco
*Assistant Examiner*—Brandon Jackson
(74) *Attorney, Agent, or Firm*—Ropes & Gray LLP; James F. Haley, Jr.; Steven K. Mossey

(57) ABSTRACT

A female condom has a pouch with an open end, a closed end, and a tubular body extending longitudinally therebetween. The female condom also includes an anchor attached to and outside of the closed end of the pouch.

27 Claims, 12 Drawing Sheets

U.S. PATENT DOCUMENTS

| | | | |
|---|---|---|---|
| 6,630,759 B2 * | 10/2003 | Yamaguchi | 310/71 |
| 7,322,358 B2 * | 1/2008 | Tam et al. | 128/830 |
| 2005/0061328 A1 | 3/2005 | Reddy et al. | |
| 2006/0106327 A1 * | 5/2006 | Thielen et al. | 601/46 |

FOREIGN PATENT DOCUMENTS

| | | |
|---|---|---|
| WO | WO 2004/026168 A | 4/2004 |
| WO | WO 2004/052255 A | 6/2004 |

* cited by examiner

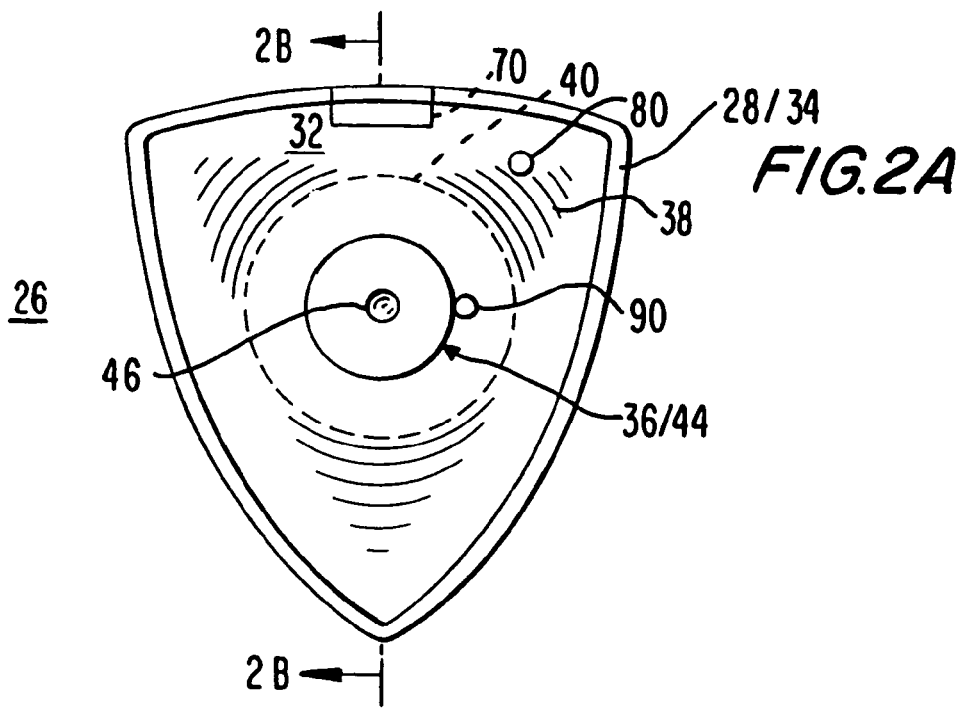
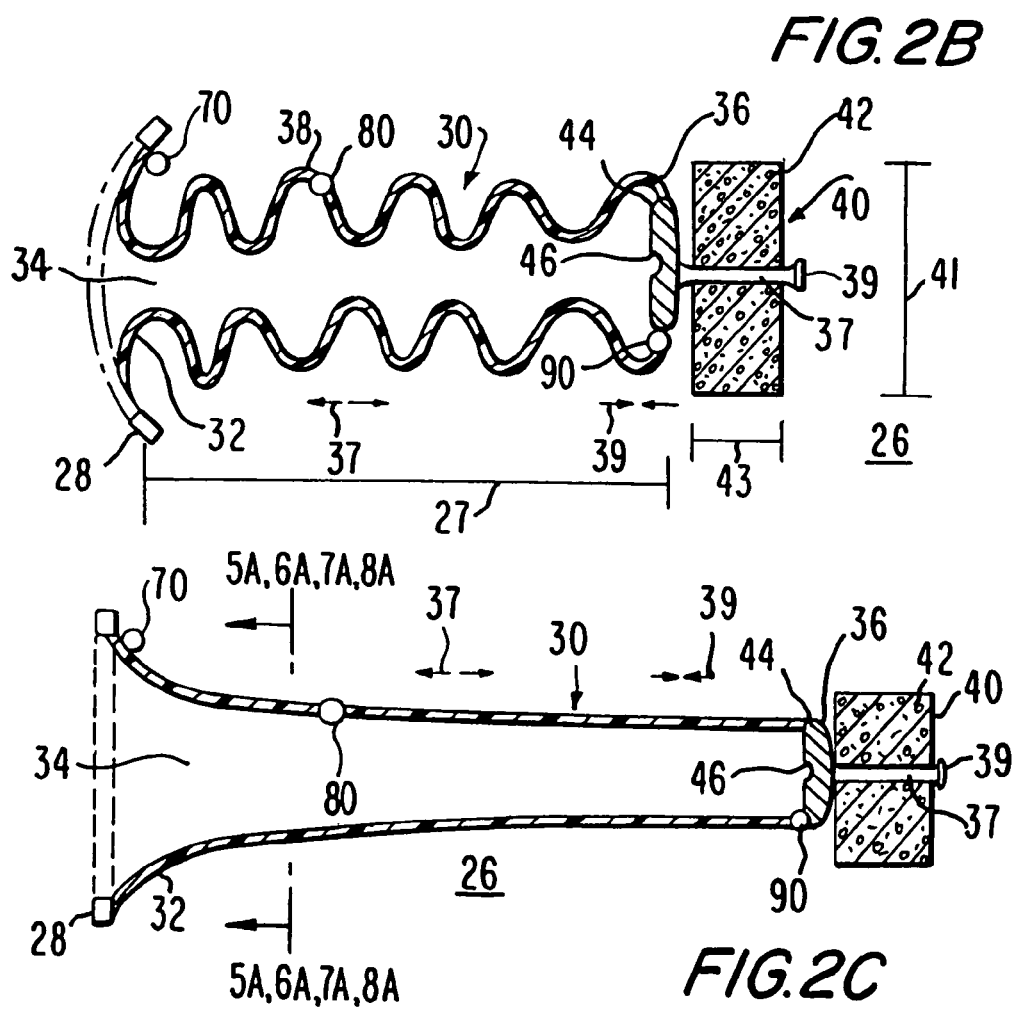

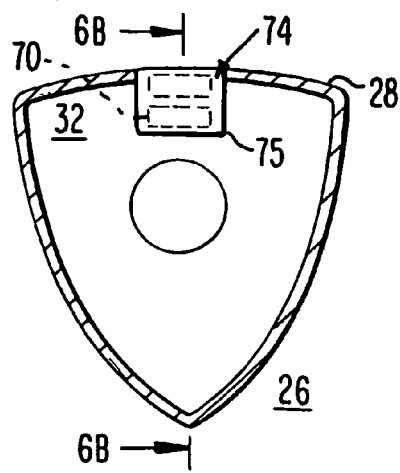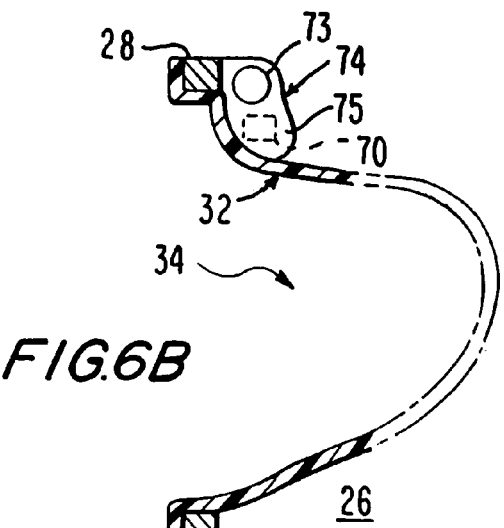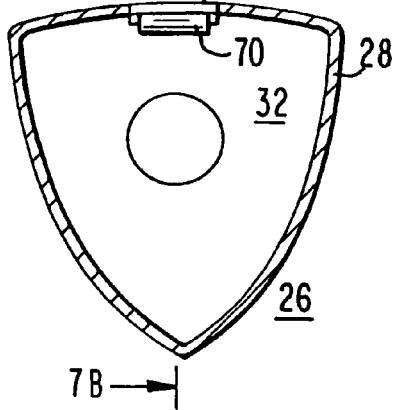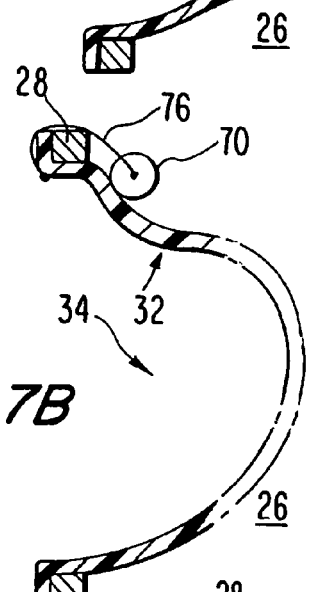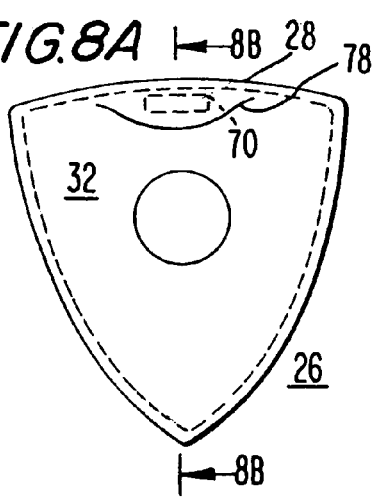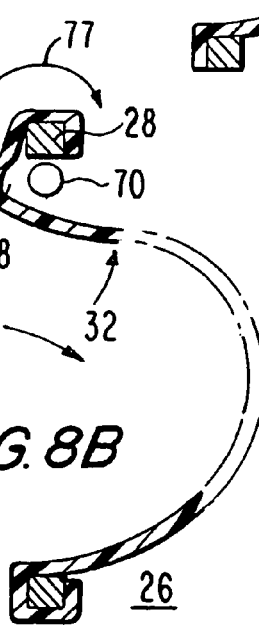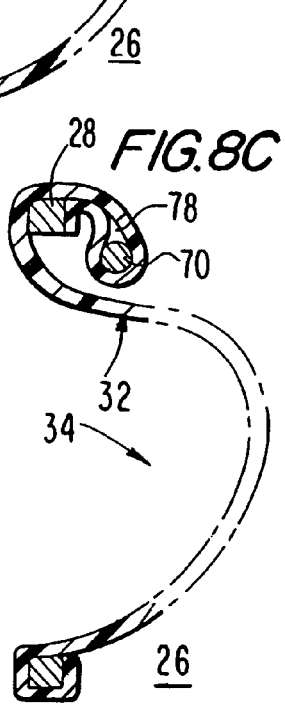

FEMALE BARRIER CONTRACEPTIVE WITH VACUUM ANCHORING

BACKGROUND OF THE INVENTION

This claims the benefit of U.S. Provisional Patent Application No. 60/664,741, filed Mar. 24, 2005, of U.S. Provisional Patent Application No. 60/676,887, filed May 2, 2005, of U.S. Provisional Patent Application No. 60/678,826, filed May 6, 2005, of U.S. Provisional Patent Application No. 60/700,853, filed Jul. 21, 2005, and of U.S. Provisional Patent Application No. 60/705,269, filed Aug. 4, 2005, each of which is hereby incorporated by reference herein in its entirety.

FIELD OF THE INVENTION

This invention relates generally to prophylactic devices and, more particularly, to female condoms with a pouch portion and a pouch retention device.

BACKGROUND OF THE INVENTION

With the proliferation of sexually transmitted diseases (STDs), including acquired immune-deficiency syndrome (AIDS), there is an increasing need for effective means to prevent the exchange of bodily fluids during sexual intercourse and the resultant transmission of STDs. One method for accomplishing this goal is by introducing an effective barrier between the male and female sex organs during sexual intercourse. Heretofore, conventional means for creating such barriers have included the use of male condoms, diaphragms, prophylactic gels, creams, and the like.

Additionally, there have been proposals to provide female prophylactic devices that can be worn by a female prior to sex and disposed of following use (i.e., a female version of a condom, generally including a pouch with a closed end that is inserted intravaginally before sexual intercourse and a retention device for securing the pouch in place to prevent withdrawal during use). While such proposals are suitable for their intended purpose, it has been found that they are not totally effective for various reasons.

One reason that the female condoms currently available have not achieved widespread use and acceptance is that they fail to adequately secure themselves in place so as to prevent withdrawal while in use. During sexual intercourse, the outward stroke of the erect penis tends to dislodge the condom pouch and pull it out of the vaginal canal as the result of creating negative pressure between the closed end of the pouch and the tip of the penis. This negative pressure results in the closed end of the condom being drawn out of the vagina during the outward stroke of the penis.

Another reason that now available female condoms are not totally effective is that they fail to provide adequate protection during sexual intercourse in different positions. For example, the length of the vaginal canal changes depending upon the position of the female partner during intercourse—in the prone position (i.e., woman on top), for instance, the vaginal canal length is shorter because the suspended cervix moves anterior, whereas in the supine position (i.e., woman on bottom) the vaginal canal length is longer because the cervix moves to the posterior position. Existing female condoms are not designed to change their length to correspond with the change in length of the vaginal canal during intercourse, thereby causing failures and inconveniences.

A third reason that female condoms now available have not become widely used and accepted is that they do not enhance, and rather they usually diminish, the pleasure attained by each partner during sexual intercourse.

Accordingly, it would be advantageous to be able to provide a female condom that is securely retained within the vagina, that is variable in length, and that may also provide stimulation to a sexual organ during sexual intercourse.

SUMMARY OF THE INVENTION

It is an object of this invention to provide a female condom that is securely retained within the vagina, that is variable in length, and that may also provide stimulation to a sexual organ during sexual intercourse.

In accordance with the invention, there is provided a female condom that includes a pouch. The pouch has an open end, a closed end, and a tubular body extending longitudinally between the open end and the closed end. The tubular body has a wall with an interior and an exterior. The female condom of this invention also includes an anchor that is coupled to the closed end of the pouch and that is positioned outside of the pouch, extending longitudinally away from the tubular body at the closed end. The anchor is capable of forming a vacuum between a wall of a vagina into which the condom is inserted and the exterior of the tubular body.

BRIEF DESCRIPTION OF THE DRAWINGS

The above and other advantages of the invention will be more apparent upon consideration of the following detailed description, taken in conjunction with the accompanying drawings, in which like reference characters refer to like parts throughout, and in which:

FIG. 2A is a front elevational view of the female condom of FIG. 1, taken from line 2A-2A of FIG. 1, but with the pelvic region omitted;

FIG. 2B is a partial cross-sectional view of the female condom of FIGS. 1 and 2A, in its original contracted configuration, taken from line 2B-2B of FIG. 2A;

FIG. 2C is a partial cross-sectional view of the female condom of FIGS. 1-2B, similar to FIG. 2B, but in its elongated position;

FIG. 6A is a rear elevational view of the female condom of FIGS. 1-4C, taken from line 6A-6A of FIG. 2C, illustrating a second embodiment of a stimulator coupling according to the invention;

FIG. 6B is a partial cross-sectional view of the female condom of FIGS. 1-4C and 6A, taken from line 6B-6B of FIG. 6A;

FIG. 7A is a rear elevational view of the female condom of FIGS. 1-4C, taken from line 7A-7A of FIG. 2C, illustrating a third embodiment of a stimulator coupling according to the invention;

FIG. 7B is a partial cross-sectional view of the female condom of FIGS. 1-4C and 7A, taken from line 7B-7B of FIG. 7A;

FIG. 8A is a rear elevational view of the female condom of FIGS. 1-4C, taken from line 8A-8A of FIG. 2C, illustrating a fourth embodiment of a stimulator coupling, in an initial coupling stage, according to the invention;

FIG. 8B is a partial cross-sectional view of the female condom of FIGS. 1-4C and 8A, in the initial coupling stage of FIG. 8A, taken from line 8B-8B of FIG. 8A;

FIG. 8C is a partial cross-sectional view of the female condom of FIGS. 1-4C, 8A, and 8B, similar to FIG. 8B, but in a subsequent coupling stage, according to the invention;

DETAILED DESCRIPTION OF THE INVENTION

The invention provides a female condom having a pouch with an open end, a closed end, and a tubular body extending longitudinally between the open end and the closed end. The female condom of this invention also includes an anchor coupled to the closed end of the pouch. The anchor is located outside of the pouch and extends longitudinally away from the tubular body at the closed end of the pouch. We believe that the anchor is capable of allowing a vacuum to form between a wall of a vagina into which the condom is inserted and the exterior of the tubular body. Preferably, the anchor is compressed during the insertion of the condom into the vagina so as to form the vacuum by expelling fluid from within the anchor to outside the vagina.

The condom preferably includes a frame with an orifice therethrough. The open end of the condom is preferably coupled to the frame about its orifice to provide a passageway into the interior of the tubular body. The frame preferably contacts the female anatomy external to the vagina upon insertion of the condom into the vagina. The vacuum capable of being created by the compressed anchor preferably pulls the frame towards the anchor. The tubular body is preferably elastic so as to change in length in consonance with the length of the vaginal canal as it varies during sexual intercourse and the thrust of the penis. The frame may also include a pocket that aligns with the clitoris of the female when the frame contacts the female anatomy external to the vagina upon insertion of the condom into the vagina. The frame also preferably includes a stimulating device within the pocket to stimulate the clitoris during use of the condom.

The invention will now be described with reference to FIGS. 1-15.

Figure 1:
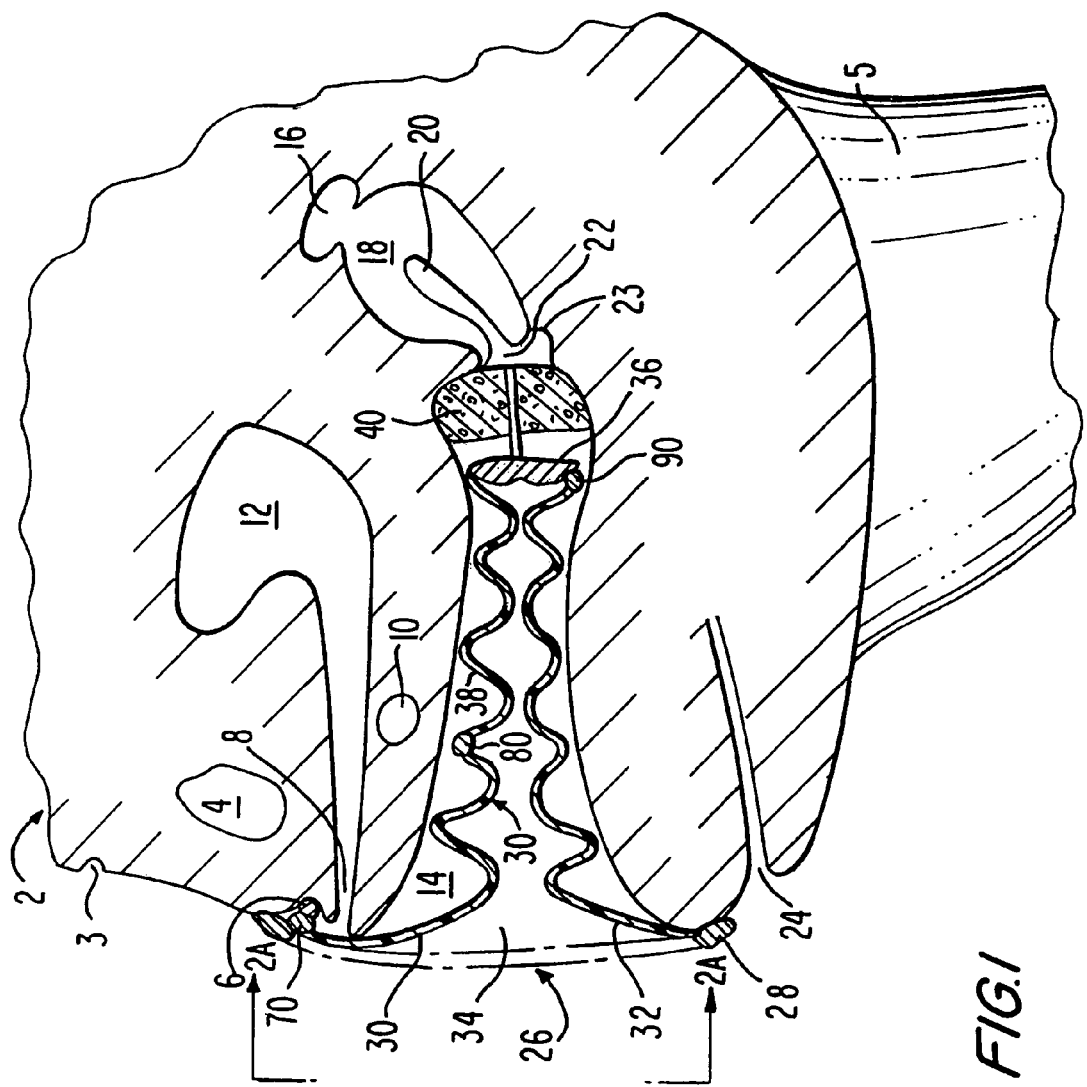
FIG. 1 is a partial cross-sectional view of a female's pelvic region showing inserted therein one embodiment of a female condom according to the invention.

FIG. 1 illustrates a cross-sectional view of a female pelvic region 2 showing the relative locations of the navel 3, pubic bone 4, leg 5, clitoris 6, urethra 8, Grafenberg spot (G-spot) 10, bladder 12, vagina 14, fallopian tube 16, uterus 18, endometrial cavity 20, cervix 22, posterior fornix 23, and rectum 24. A preferred embodiment of a female condom 26 according to the invention is inserted in the canal of vagina 14.

As also illustrated in FIGS. 2A-4C, condom 26 includes an outer frame 28 with an orifice therethrough. Frame 28 may be formed in any desired suitable shape that allows the frame to contact the female anatomy external to vagina 14 about the vaginal opening. Preferably, frame 28 is formed as an anatomically designed triangle or such geometric shape, as shown in FIG. 2A. In its contracted configuration, as illustrated in FIG. 2B, for example, frame 28 may also be contoured in a curved or dome-like manner so as to better conform to the female anatomy external to vagina 14. This contour of frame 28 is generally concave on the side of frame 28 that contacts the female anatomy external to vagina 14 (see, e.g., FIG. 1). Frame 28 may be formed of any suitable resilient polymeric material that has sufficient flexibility to be easily deformed, but that also is stiff and resilient enough to have a spring bias for returning frame 28 to its original contracted configuration following removal of any deforming pressure. Preferred material to be used for the frame besides plastic may be rubber, thermoplastic elastomers, or similar matter, for example. Frame 28 may be formed by injection molding or any other suitable means well known in the art, such as by inserting a flexible stiffener rod inside an extruded tube assembly whose ends are joined and shaped to the desired configuration.

Condom 26 also includes a pouch 30 having an open end 34, a closed end 36, and a resilient tubular body portion 32 that extends longitudinally between open end 34 and closed end 36. Pouch 30 may be coupled at its open end 34 to frame 28 by rolling and bonding, molding, heat-sealing, adhering, or any other known method. Preferably, open end 34 of pouch 30 is attached to frame 28 by a simple roll-on operation such that the tubular body portion 32 proximal to open end 34 is rolled at least three times about frame 28.

Tubular body portion 32 of pouch 30 is preferably formed from any suitable elastic and impermeable membrane material, such as natural rubber (e.g., latex), synthetic rubber (e.g., silicone rubber or neoprene), polyurethane, and other elastic substances (e.g., thermoplastic polyolefin elastomers), for example. Other useful materials for tubular body portion 32 include non-elastic substances such as various thermoplastic materials (e.g., polyethylene). A plurality of bellows-like convolutions or corrugations 38 are preferably formed along the length of tubular body portion 32 to increase the elasticity of pouch 30, while also providing stimulation to the penis during sexual intercourse and enabling conformance of pouch 30 to the wall of vagina 14. Convolutions 38 are preferably circular and are formed to act in a spring-like manner, whereby if pouch 30 is extended in the longitudinal direction (i.e., along the major length of pouch 30 in the direction of arrows 37) into an elongated configuration (see, e.g., FIG. 2C), by the insertion of a penis or the like, pouch 30 will return to its original non-extended configuration (see, e.g. FIG. 2B) following withdrawal of the penis due to a spring-like bias in the longitudinal direction (i.e., along the major length of pouch 30 in the direction of arrows 39).

Condom 26 also includes an anchor 40 that is coupled to and outside of the closed end 36 of pouch 30 and extends longitudinally away from tubular body portion 32 at closed end 36. Anchor 40 may be coupled to closed end 36 of pouch 30 mechanically, or by molding, heat-sealing, adhering, or any other known method. In the preferred embodiment shown in FIGS. 1-2C, a joiner portion 37 of pouch 30 is coupled to and extends from closed end 36, through anchor 40, and is held by a smaller anchor 39 that locks itself into larger anchor 40.

Anchor 40 may preferably be formed of any suitable compressible and resilient mass or porous sponge-like material, such as natural sponge material or a suitable, soft, porous sponge-like natural or synthetic material having voids or cells (e.g., cells 42). Suitable materials, include natural sponge material, soft rubber open lattice material, polyurethane latex foam of the open cell blown type, and the like, that can be compressed into a compact shape and that are resiliently expandable upon absorption of fluid, as described in more detail below. The voids or porous cells 42 can be impregnated with lubricant, spermicides, fungicides, bactericides, or antiviral agents that can be slowly released therefrom to protect a user, as desired.

Anchor 40 may be a sponge or, alternatively a suction cup device, of any suitable size and shape, such as U-shaped, V-shaped, or cylindrical, for example, and may be provided with a smooth but apertured coating, such as polyurethane or latex, to reduce or prevent any abrasion that may result on vagina 14 due to contact with anchor 40.

In the preferred embodiment illustrated in FIGS. 1-4C, anchor 40 is cylindrical and is provided with porous cells 42 of various sizes. The diameter 41 (see, e.g., FIG. 2B) of anchor 40 may be larger, smaller, or the same as the diameter of pouch 30 such that it may be inserted comfortably into the canal of vagina 14 and retained near cervix 22 at the posterior fornix 23, as described in more detail below. Anchor 40 may preferably have a thickness 43 (see, e.g., FIG. 2B) between one half inch and two and a half inches, for example, in order to obtain the desired length of condom 26 when anchor 40 is compressed, as described in more detail below.

Additionally, condom 26 may preferably be provided with a cushion 44 within the interior of tubular body portion 32 of pouch 30 at closed end 36. Cushion 44 may be any suitable compressible material, such as a porous sponge like the material of anchor 40, for example, and may be coupled to the pouch by being inserted in a recess at the closed end of the pouch. Cushion 44 may be compressed by the tip of a penis on its inward strokes during sexual intercourse, such that upon the following outward strokes of the penis, no or only a minimal vacuum is created between the tip of the penis (i.e., the glans penis 51) and closed end 36 of pouch 30, as described in more detail below (see, e.g., FIGS. 4B and 4C). A smooth but apertured thin membrane coating made of any suitable material, such as polyurethane or latex, may cover cushion 44 to reduce or prevent any abrasion that may result on the penis due to contact with cushion 44. Cushion 44 may also preferably have an insertion indentation 46 formed in the outer surface of cushion 44 facing open end 34 of pouch 30. Insertion indentation 46 is preferably configured to receive a finger of a user to facilitate insertion of condom 26 in vagina 14 so that no separate insertion tool is required (see, e.g., FIGS. 3 and 4A). Furthermore, cushion 44 may ensure that a user's finger does not accidentally penetrate closed end 36 of pouch 30 during insertion of condom 26 into vagina 14 or by a penis during sexual intercourse.

Figure 3:
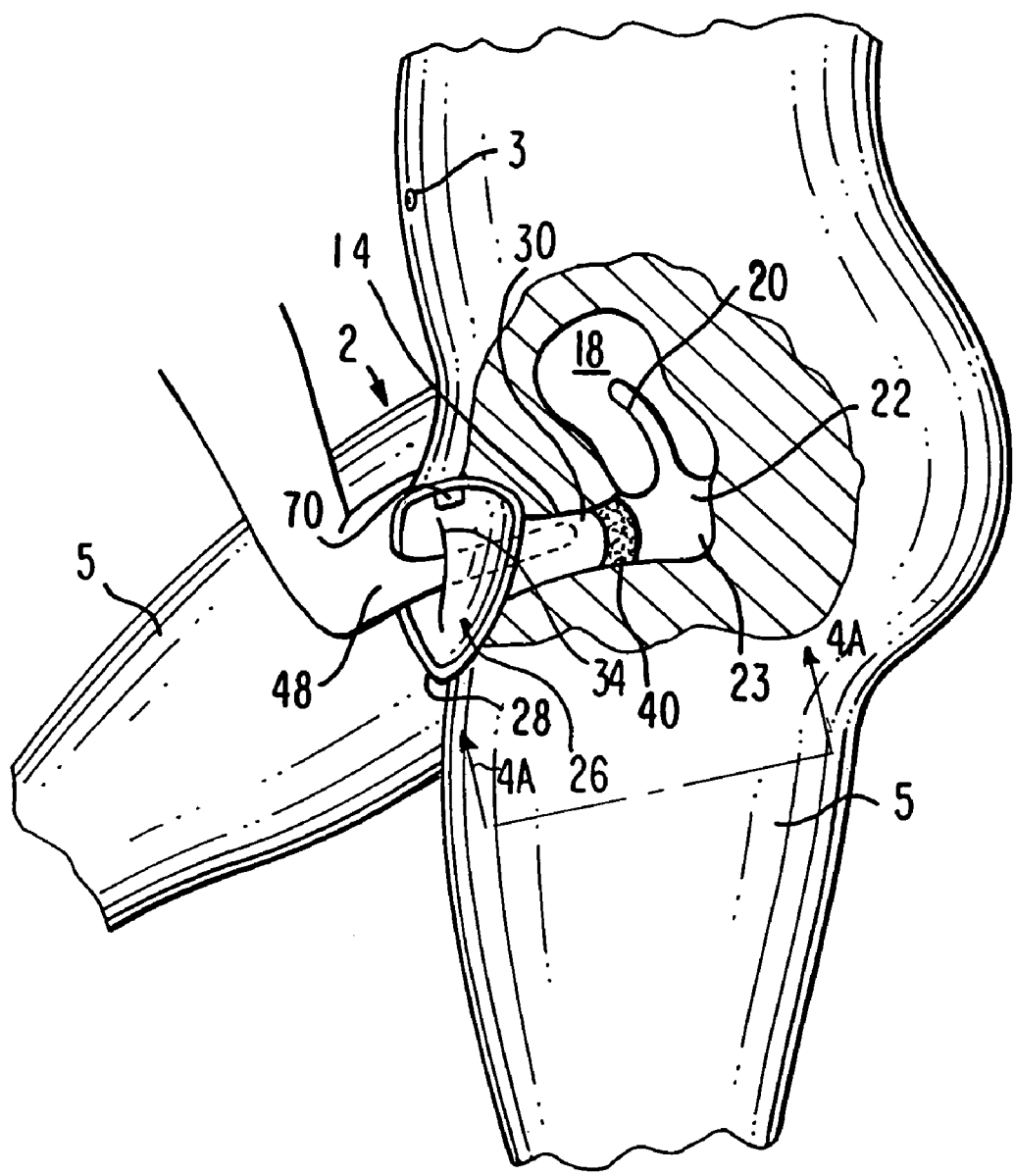
FIG. 3 is a partially sectional perspective view of the female condom of FIGS. 1-2C in a stage of an insertion procedure of the condom into the pelvic region of FIG. 1, according to the invention.

Thus, condom 26 may be inserted into vagina 14, and positioned as illustrated in FIGS. 1 and 3, by inserting, and preferably by rotating, one or more fingers 48 through the orifice of frame 28 and open end 34 of pouch 30, and into the interior of tubular body portion 32, and by pushing closed end 36 and anchor 40 into the canal of vagina 14, as illustrated in FIG. 3. The tip of at least one finger 48 may push anchor 40 against cervix 22 at the end of the canal of vagina 14 near posterior fornix 23 such that anchor 40 compresses and expels fluid therefrom, thereby creating a vacuum between the wall of vagina 14 and the exterior of tubular body portion 32 so as to retain anchor 40 and closed end 36 of condom 26 within vagina 14, as described in more detail below (see, e.g., FIGS. 4A-4C).

Figure 4A:
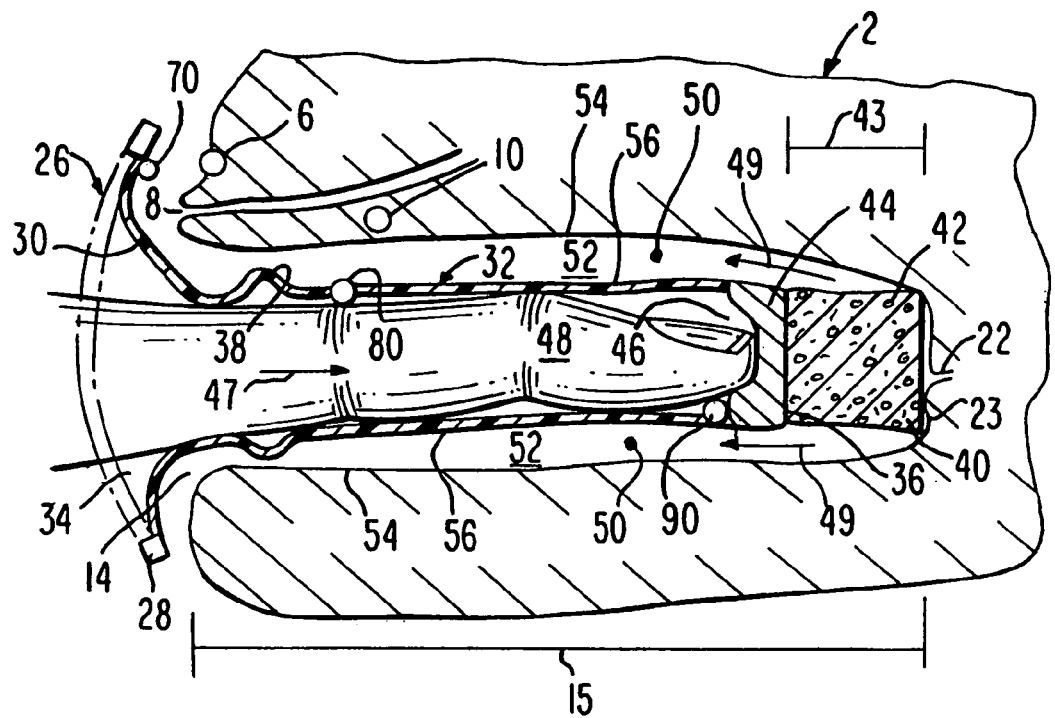
FIG. 4A is a partial cross-sectional view of the female condom of FIGS. 1-3, in the insertion procedure stage of FIG. 3, taken from line 4A-4A of FIG. 3.

As shown in FIG. 4A, when finger 48 pushes closed end 36 and anchor 40 through the canal of vagina 14 in the direction of arrow 47, preferably by contacting indentation 46 of cushion 44, anchor 40 compresses against the end of the canal, preferably at cervix 22. This compression of anchor 40 causes any fluid 50 previously absorbed by or contained in anchor 40, such as air or any natural juices within vagina 14, to be expelled in the direction of arrows 49, not only from anchor 40, but also from vagina 14, through a passageway 52 defined by wall 54 of vagina 14 and the exterior wall 56 of tubular body portion 32 of condom 26.

Figure 4B:
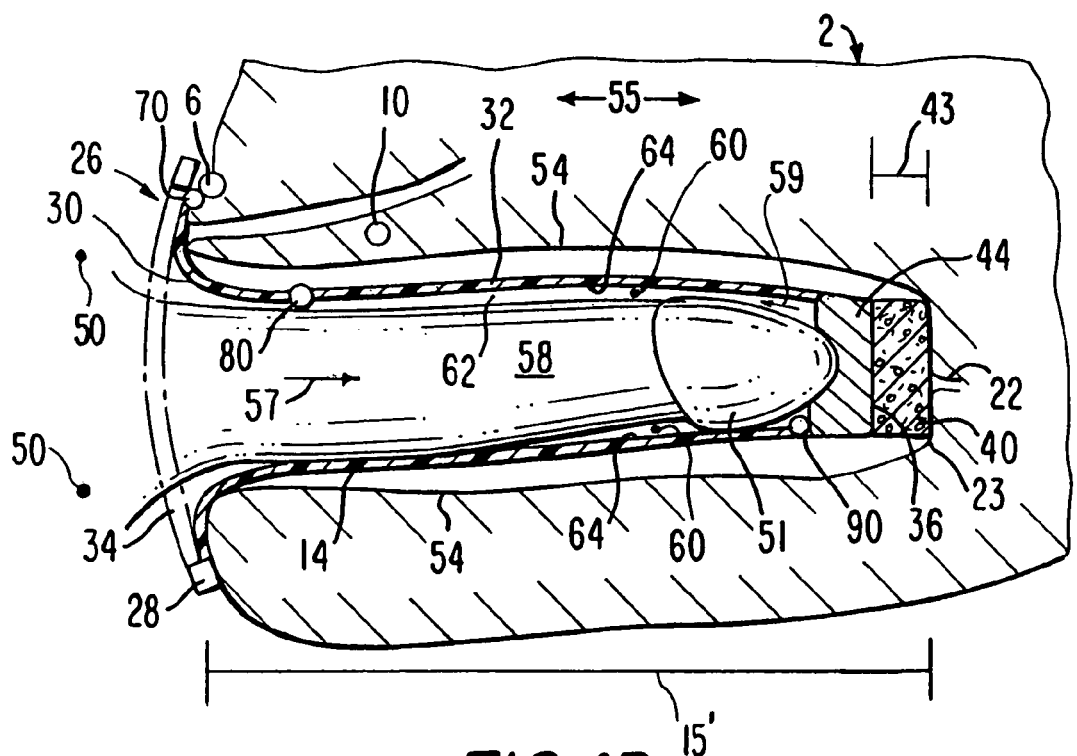
FIG. 4B is a partial cross-sectional view of the female condom of FIGS. 1-4A, similar to FIG. 4A, but in a first stage of use within the pelvic region of FIGS. 1, 3, and 4A, according to the invention.

Due to this expulsion of fluid 50 from vagina 14, the pressure within passageway 52 drops and creates at least a partial vacuum therein, while the compression of anchor 40 reduces its original thickness 43 (see, e.g., FIGS. 2B and 4A) to a compressed thickness 43' (see, e.g., FIG. 4B). This vacuum in combination with the reduced thickness of anchor 40 pulls frame 28 in the direction of arrow 47 towards anchor 40 and against the female anatomy external to vagina 14, as shown in FIG. 4B, thereby preventing any fluid 50 from re-entering vagina 14 and being re-absorbed by anchor 40, such that the vacuum is maintained so as to retain compressed anchor 40 against the end of the canal of vagina 14.

Lubrication may preferably be provided on exterior wall 56 of tubular body portion 32 to act as an effective sealant with wall 54 of vagina 14, thereby assisting in maintaining the vacuum. Any suitable lubrication may be used for this purpose, but the type of lubrication preferably varies depending on the material used to form tubular body portion 32. For example, silicon oil lubricant may be preferable in conjunction with a tubular body made of latex, while mineralized oil may be the preferable lubrication for use with a thermoplastic tubular body. Lubrication may preferably also be provided on the interior wall of tubular body portion 32 to provide for comfortable penetration of an erect penis during sexual intercourse.

Once anchor 40 has been pushed and compressed against the end of the canal of vagina 14, open end 34 of condom 26 may then receive a penis to initiate sexual intercourse. In a preferred embodiment, as described above, open end 34 initially starts as a generally triangular opening due to the shape of frame 28 (see, e.g., FIG. 2A), and transitions into tubular body 32, which is shown in a circular or cylindrical shape in the preferred embodiment, but which may be any desired cross-sectional shape. Furthermore, as described above, convolutions 38 may preferably be formed along the length of tubular body 32, and may serve to retain condom 26 in its original contracted configuration (see, e.g., FIG. 2B), while also providing stimulation to a penis during sexual intercourse and enabling conformance of pouch 30 to the wall of vagina 14 before and during intercourse. A normal vaginal canal is generally two to three inches in length, but penetration by a penis during sexual intercourse can increase the length of the vaginal canal to six or seven inches depending on the anatomy of the sexual organs of the partners. Preferably, tubular body portion 32 of condom 26 is constructed to have a longitudinal length 27 in its original contracted configuration (see, e.g., FIG. 2B) that is equal to or shorter than the longitudinal length 15 of the canal of vagina 14 prior to insertion of a penis (see, e.g., FIG. 4A).

As illustrated in FIG. 4B, when a penis 58 is inserted into open end 34 of condom 26 during sexual intercourse, penis 58 will inwardly thrust into vagina 14 in the direction of arrow 57, thereby preferably contacting cushion 44. This inward thrust of penis 58 will either further compress anchor 40 and/or push the fully-compressed anchor 40 further into vagina 14, depending on whether or not penetration of penis 58 increases the longitudinal length 15 of the canal of vagina 14 (i.e., to length 15' of FIG. 4B). Any additional compression of anchor 40 by the inward thrust of penis 58 preferably causes any remaining fluid 50 previously absorbed by anchor 40 to be expelled from within anchor 40 and vagina 14 (as described above with respect to FIG. 4A).

As shown in FIG. 4B, when anchor 40 is pushed further into vagina 14 by the inward thrust of penis 58, convolutions 38 and/or simply the resiliency and elasticity of the material of tubular body 32 enable pouch 30 to stretch in the direction of arrows 55 to its elongated configuration (also see, e.g., FIG. 2C). Thus, in the same manner as the vaginal canal elongates during sexual intercourse, pouch 30 will also elongate. Similarly, when the vaginal canal shortens due to withdrawal of the penis, pouch 30 will also shorten (see, e.g., FIG. 4C) in the longitudinal direction opposite to the direction of arrows 55.

With further reference to FIG. 4B, during its inward thrust in the direction of arrow 57, penis 58 may preferably compress cushion 44 against closed end 36 and anchor 40. This compression of cushion 44 not only may provide comfort to the tip of penis 58, but also may preferably cause any fluid 60 that had previously been absorbed by cushion 44 to be expelled from cushion 44 in the direction of arrows 59 into a passageway 62 defined by penis 58 and the interior wall 64 of tubular body portion 32 of condom 26.

Figure 4C:
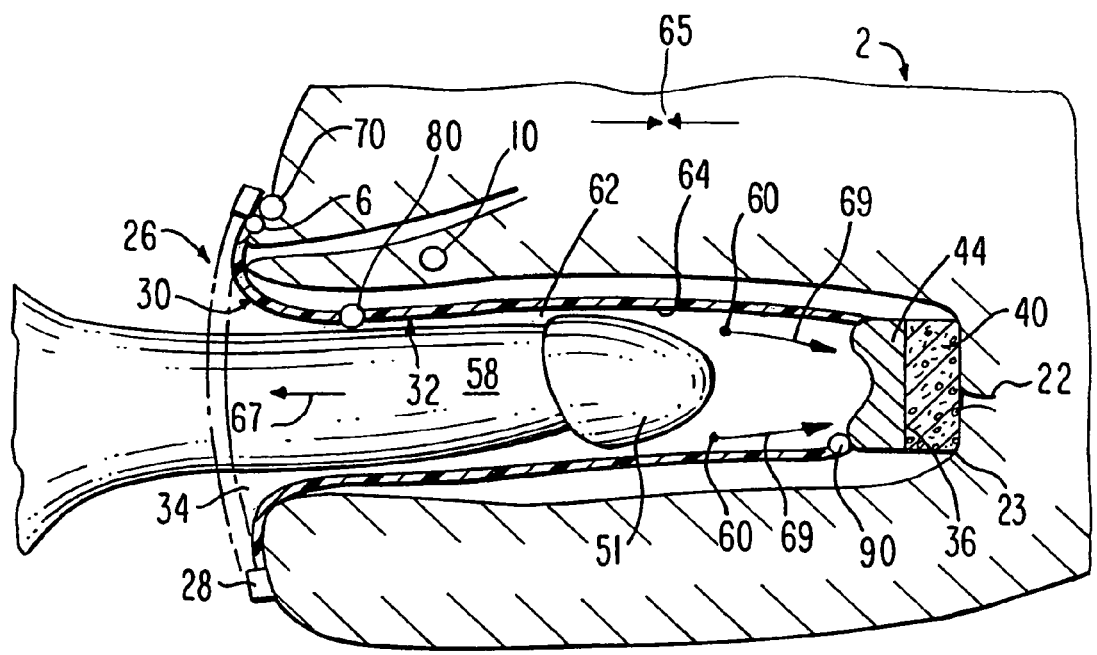
FIG. 4C is a partial cross-sectional view of the female condom of FIGS. 1-4B, similar to FIGS. 4A and 4B, but in a second stage of use within the pelvic region of FIGS. 1 and 3-4B, according to the invention.

As illustrated in FIG. 4C, penis 58 is at least partially withdrawn from open end 34 of condom 26 by an outward thrust from vagina 14 in the direction of arrow 67 during sexual intercourse, thereby preferably decompressing cushion 44 at least partially. This decompression of cushion 44 preferably allows for fluid 60 to be re-absorbed by cushion 44 in the direction of arrows 69, thereby preventing any substantial negative pressure to be created between the tip of penis 58 and closed end 36 of condom 26 during the outward stroke of penis 58 that could have overpowered the vacuum created by anchor 40 and thus loosened anchor 40 from its retained state. As the vaginal canal shortens due to withdrawal of penis 58, convolutions 38 and/or simply the resiliency and elasticity of the material of tubular body 32 enable pouch 30 to retract in the direction of arrows 65 back towards its original contracted configuration (also see, e.g., FIG. 2B).

The elasticity of pouch 30 greatly increases the longitudinal retractive bias of condom 26 for returning the condom to its original contracted configuration. This longitudinal spring bias in combination with the retention properties of anchor 40 allows frame 28 to remain in contact with the female anatomy external to vagina 14, not only when the vaginal canal is elongated during the inward thrust of penis 58 (see, e.g., FIG. 4B), but also when the vaginal canal is shortened due to at least partial withdrawal of the penis (see, e.g., FIG. 4C).

Frame 28 may also preferably have a spring-biased contour associated with it, as described above with respect to FIG. 2B. This spring-based contour may not only enable frame 28 to flex, so as to better retain contact with the female anatomy external to vagina 14 when condom 26 is inserted in vagina 14, but it may also enable and provide additional contractive bias to pouch 30 in the longitudinal direction. Frame 28 is preferably sufficiently resilient to flatten out during penetration by the male for providing more intimate contact during intercourse, as illustrated in FIGS. 2C and 4B, and then to return to its original contoured shape following withdrawal of the penis, as illustrated in FIGS. 2B and 4C.

In an alternative embodiment, the female condom of the invention may be used with a non-contoured frame, such as a flat frame, or a frame shaped in a shape other than triangular, such as circular or hexagonal.

In another alternative embodiment, the female condom of the invention may have a pouch with a non-convoluted tubular body that is formed of highly resilient latex or a similar material capable of stretching at least in the longitudinal direction when a penis is inserted therein, and then springing back to the original contracted configuration when the penis is withdrawn therefrom, as mentioned above.

Furthermore, in yet another alternative embodiment, the female condom of the invention may have an anchor that is not a cylinder of porous sponge-like material, but is instead a plastic or rubber cup-shaped device that adheres to the end of the vaginal canal by means of suction.

In a preferred embodiment of the invention, one or more stimulating devices may be coupled to the female condom for providing stimulation to one or more sexual organs of one or both of the partners to enhance the pleasure felt during sexual intercourse. Various types of stimulating devices may be utilized at various locations on the female condom for stimulating specific sexual organs in specific ways.

In a particularly preferred embodiment of the invention, a stimulating device may be coupled to the frame of the female condom of the invention such that the stimulator aligns with the clitoris when the frame contacts the female anatomy external to the vagina on insertion of the condom into the vagina. As illustrated in FIGS. 1-4C, a stimulator 70 is preferably coupled to the side of frame 28 that contacts the female anatomy external to vagina 14, although the stimulator may be coupled to the opposite side or provided within frame 28 in other embodiments. Once anchor 40 is retained within vagina 14, frame 28 is in contact with the female anatomy external to the vagina, as described above. Therefore, stimulator 70 may be positioned on frame 28 so as to provide continuous stimulation to clitoris 6 for the entire period of time condom 26 is in use. This is particularly beneficial because the female may continue to be stimulated after her partner's penis has become flaccid and completely removed from pouch 30 of condom 26.

Furthermore, as described above, frame 28 is preferably sufficiently resilient to flatten out during penetration by the male thus providing more intimate contact during intercourse, as illustrated in FIGS. 2C and 4B, and then returning to its original contoured shape following withdrawal of the penis, as illustrated in FIGS. 2B and 4C. This flexing of frame 28 during sexual intercourse may vary the proximity of stimulator 70 to clitoris 6, thereby varying the amount of stimulation provided by stimulator 70 to clitoris 6 in harmony with the inward and outward thrusts of the penis.

Figure 5A:
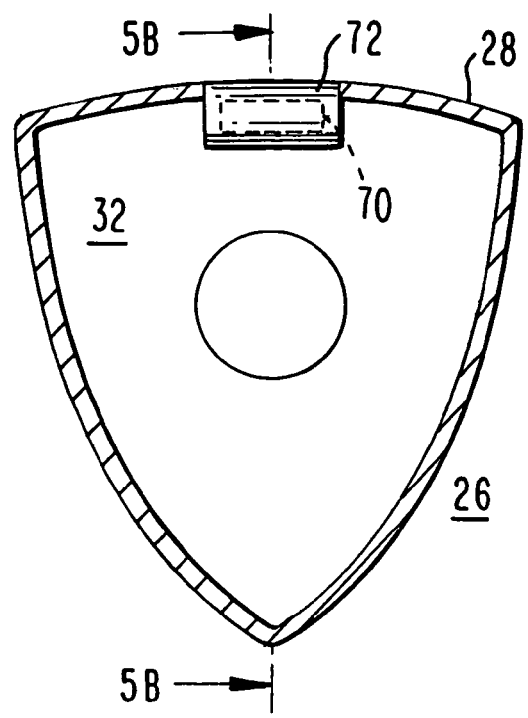
FIG. 5A is a rear elevational view of the female condom of FIGS. 1-4C, taken from line 5A-5A of FIG. 2C, illustrating a first embodiment of a stimulator coupling according to the invention.
Figure 5B:
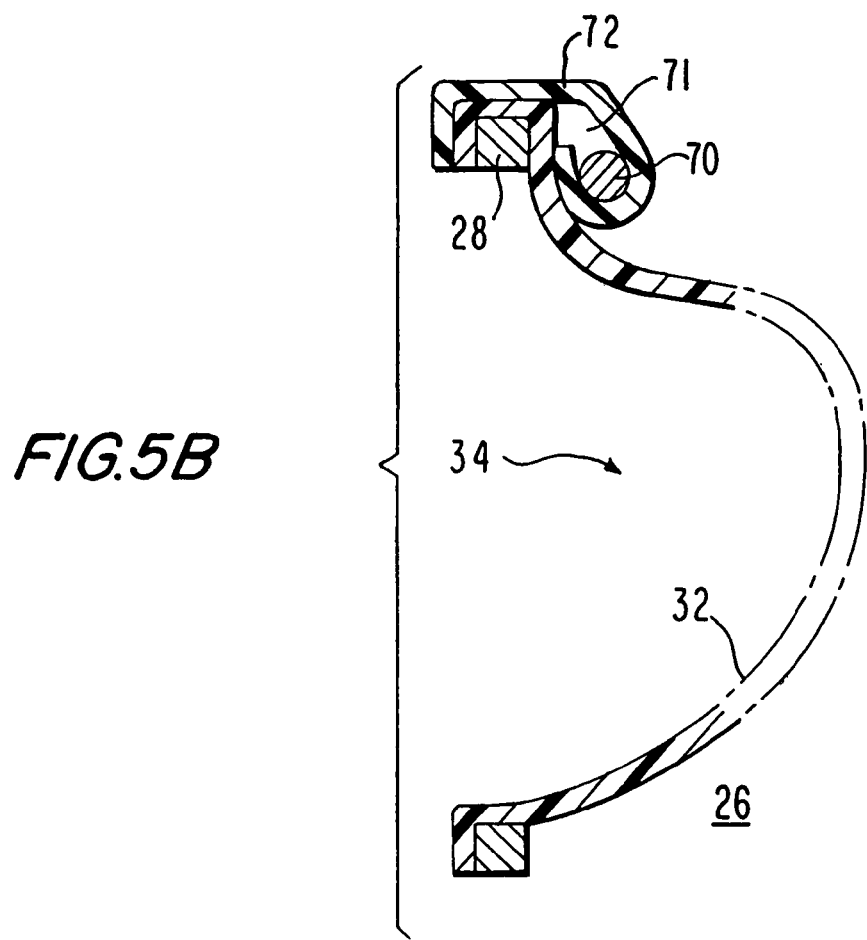
FIG. 5B is a partial cross-sectional view of the female condom of FIGS. 1-5A, taken from line 5B-5B of FIG. 5A.

Stimulator 70 may be coupled to frame 28, as described above, by various means. In one embodiment, as shown in FIGS. 5A and 5B, a loop 71 is provided by a preferably rectangular strip 72 for holding stimulator 70 therewithin during sexual intercourse. Strip 72 may be made of any suitable material, such as thin rubber or polyurethane film, and may be coupled to frame 28 to create loop 71 by any suitable process, such as by rolling strip 72 about frame 28 along with open end 34 of condom 26, or by attaching strip 72 to frame 28 by adhesives or mechanical clips, for example. Stimulator 70 may preferably be slid into and held by loop 71 such that stimulator 70 provides stimulation during sexual intercourse. Therefore, stimulator 70 may be held within loop 71 during use of condom 26 and then withdrawn from loop 71 after sexual intercourse such that stimulator 70 may be reused and such that condom 26 may be discarded. Alternatively, the stimulator may be a permanent part of the condom so as to be discarded along with the condom after use.

In another embodiment, as shown in FIGS. 6A and 6B, a pocket 74 may be coupled to frame 28 by any suitable process, such as dipping, heat-sealing, or joining with adhesives. Pocket 74 may preferably include an opening 73 for passing stimulator 70 therethrough and into the recess or cavity 75 formed by pocket 74. Therefore, stimulator 70 may be held within pocket 74 during use of condom 26 and then withdrawn from pocket 74 after sexual intercourse such that stimulator 70 may be reused and such that condom 26 may be discarded. Alternatively, the stimulator may be a permanent part of the condom so as to be discarded along with the condom after use.

In yet another embodiment, as shown in FIGS. 7A and 7B, a clasp 76 may be coupled to frame 28 by hooking, sealing, mechanically fixing, or any other known process. Clasp 76 may preferably be releasably connected to stimulator 70, such that stimulator 70 may be coupled to frame 28 during use of condom 26 and then released from clasp 76 after sexual intercourse such that stimulator 70 may be reused and such that clasp 76 may be discarded along with condom 26. Alternatively, clasp 76 may be releasably connected to frame 28, such that stimulator 70 and clasp 76 may be reused and such that condom 26 may be discarded. Alternatively, the stimulator and clasp may each be a permanent part of the condom so as to be discarded along with the condom after use.

In still yet another embodiment, as shown in FIGS. 8A-8C, a sack 78 may be integrated into pouch 30 near open end 34, such that stimulator 70 may be held within sack 78 during use of condom 26. As illustrated, additional material may be provided by pouch 30 to create sack 78. The user may insert stimulator 70 within sack 78 and wrap it around frame 28 in the direction of arrow 77, thereby pulling sack 78 tight around stimulator 70 and frame 28, and thereby holding stimulator 70 in the proper position for stimulation during use of condom 26. Therefore, stimulator 70 may be held within sack 78 during use of condom 26 and then withdrawn from sack 78 after sexual intercourse such that stimulator 70 may be reused and such that condom 26 may be discarded. Alternatively, the stimulator may be a permanent part of the condom so as to be discarded along with the condom after use.

As mentioned above, in addition to or instead of a clitoral stimulation device (e.g., stimulator 70) coupled to the frame, one or more stimulating devices may be coupled to any other portion of the female condom for providing stimulation to one or more other sexual organs of one or both of the partners to enhance the pleasure felt during sexual intercourse. For example, in a particularly preferred embodiment of the invention, stimulating devices may be provided along the length of the tubular body portion 32 of the pouch of the condom for stimulating the Grafenberg spot 10 of the female partner (see, e.g., stimulator 80 of FIGS. 1-4C) and at the closed end 36 of the pouch for stimulating the glans penis 51 of the male partner (see, e.g., stimulator 90 of FIGS. 1-4C), such that each stimulator may align with the respective sexual organ or organs it is to stimulate on insertion of the condom into the vagina. Stimulators provided along the length of the condom may be placed in a recess created in the pouch when molded, for example. Stimulators may also be provided within the anchor and/or the cushion of the female condom, for example.

As mentioned above with respect to clitoral stimulator 70, the positioning of G-spot stimulator 80, glans penis stimulator 90, or any other type of stimulator anywhere on the female condom preferably provides continuous stimulation to the particular sexual organ of that respective stimulator for the entire period of time that the female condom is in vagina 14. This is particularly beneficial as the female may continue to be stimulated by the stimulator or stimulators provided by the female condom even after her male partner's penis has become flaccid and completely removed from the condom.

The female condom of the invention may be provided with one or more stimulation devices that can provide stimulation to one or more sexual organs of one or both of the partners to enhance the pleasure felt during sexual intercourse. Stimulators of the invention, including clitoral stimulator 70, G-spot stimulator 80, and glans penis stimulator 90, for example, may each either be an electronic device (e.g., a battery operated vibrator) or simply a mechanical device (e.g., a flexible rubber element with protrusions) that is able to provide stimulation to a sexual organ during sexual intercourse.

In a preferred embodiment of the invention, any electronic device provided with the female condom as a stimulator preferably works on the principle of making physical contact with the user through a moving object that offers impact with the least resistance. This type of stimulator, unlike common vibrators, does not have an eccentric weight attached to a motor shaft, but instead preferably has an offset shaft attached to a rotor. The shaft can be a singular or multiple offset or non-offset shaft, and attached to the one or more shafts is preferably one or more sleeves that are able to move freely when mounted on its shaft. A power source, the motor, and its shaft or shafts are preferably contained within an outer case, and one or more openings are preferably provided in the case to enable direct contact between the sleeves and a sexual organ for the stimulation thereof.

When the motor is in operation in this preferred embodiment, each sleeve may spin around the rotor shaft and, due to centrifugal force, may be outwardly displaced until it makes contact with a fixed object (e.g., the sexual organ to be stimulated). Upon hitting the fixed object, the sleeve may preferably be forced to lessen its contact with the object, either by the sleeve deforming, by the sleeve sliding about its shaft, or by the shaft sliding itself, until the sleeve is freed of contact with the object. Once freed of contact with the fixed object, the sleeve may preferably return to its outward displacement while spinning about its shaft. This movement of the sleeve from being displaced outwardly, to being freed from contact with the fixed object, to returning to its outward displacement allows for the stimulator to contact a fixed object during every rotation of the shaft while offering the least resistance. As this contact is made with the least resistance, the energy required by the stimulator is very low and the contact with the fixed object is non-vibratory in nature.

Figure 9A:
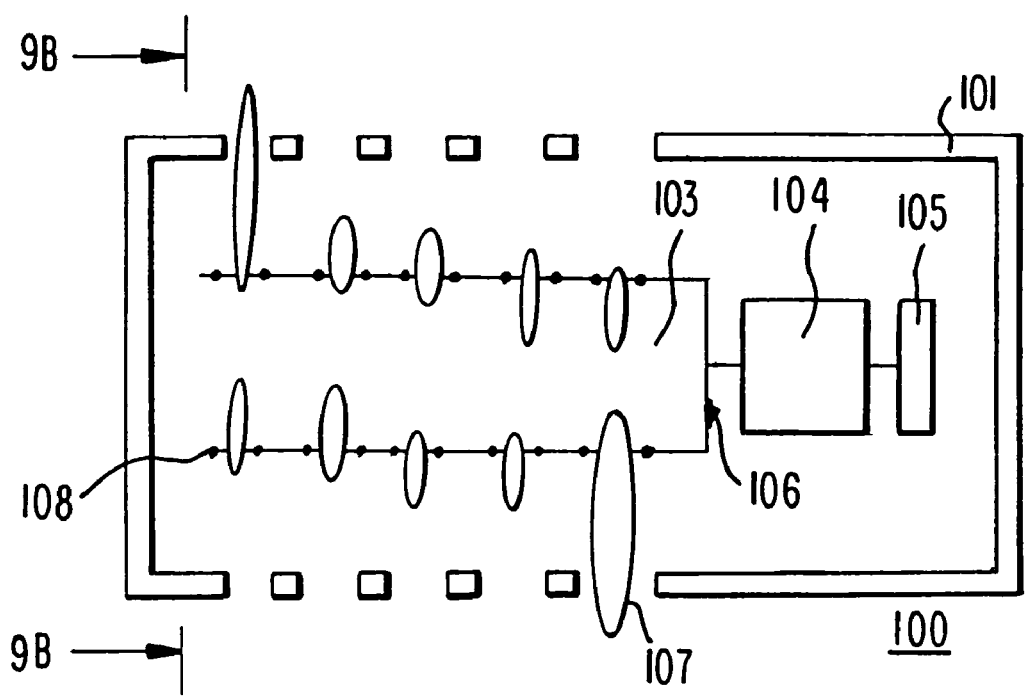
FIG. 9A is a partial cross-sectional view of a first embodiment of a stimulator according to the invention.
Figure 9B:
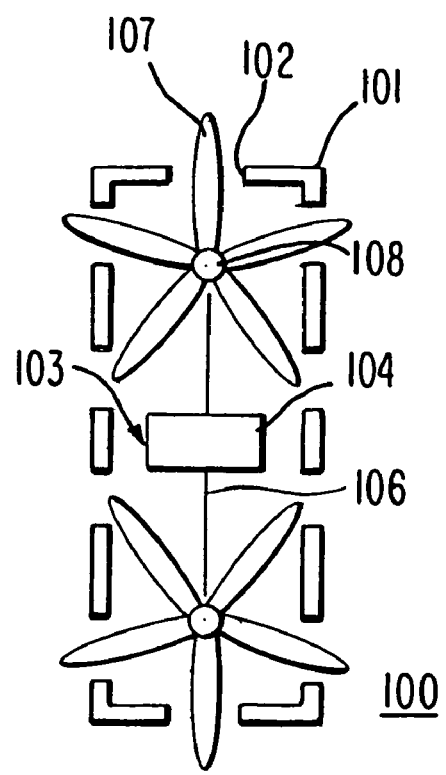
FIG. 9B is a partial cross-sectional view of the stimulator of FIG. 9A, taken from line 9B-9B of FIG. 9A.

In one embodiment, as shown in FIGS. 9A and 9B, a stimulator 100 of the invention has an outer case 101 containing therein a motor 104 that is coupled to a rotor assembly 103 and a power source 105. Rotor assembly 103 preferably includes a double offset shaft fixture 106 mating the rotor of motor 104. Each offset shaft 106 preferably has one or more outwardly displaceable sleeves 107 that may be held in position thereon by one or more stoppers 108. When motor 104 starts drawing power from power source 105, the rotor may start rotating shafts 106 to let sleeves 107 occupy their outward position, thereby preferably forming a fan-like structure (see, e.g., FIG. 9B), which has restricted access through openings 102 in case 101 to provide direct contact with a sexual organ for stimulation thereof.

Figure 10:
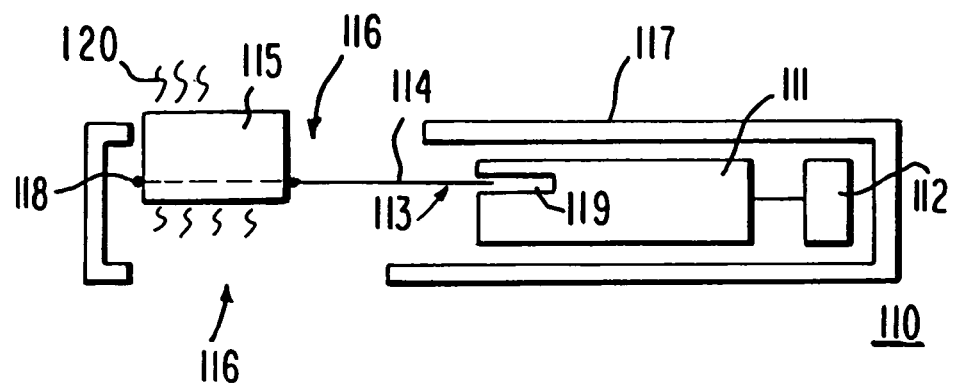
FIG. 10 is a partial cross-sectional view, similar to FIG. 9A, of a second embodiment of a stimulator according to the invention.

An alternative embodiment of a stimulator 110 is shown in FIG. 10, where a motor 111 is connected to a power source 112 and a rotor assembly 113 by a non-offset shaft 114 extending out to accommodate a sleeve 115. Sleeve 115 may be hollow and may move outwardly through opening 116 in case 117 as the rotor starts rotating, but may be prevented from moving completely off of shaft 114 by a stopper 118. Additionally, the end of shaft 114 may extend from a slot 119, whereby as the shaft rotates, sleeve 115 rotates but will cause shaft 114 to slide back along slot 119 upon impact with the anatomy to be stimulated.

In certain preferred embodiments, the sleeves are provided as flexible pads that are integral parts of a shaft, such that as the shaft rotates, the flexible pads rotate but will bend or give way to resistance upon impact with the anatomy to be stimulated. Any suitable material may be used to form these flexible pads or any of the sleeves described above, such as foam, PVC, rubber, polypropylene, polyurethane, or any combination thereof, for example. Extensions, such as bristles 120 shown in FIG. 10, may be formed upon each sleeve to provide the flexibility for impacting the anatomy to be stimulated with the least resistance.

In an alternative embodiment of the invention, a female condom may be provided as an integral part of a bikini bottom or female undergarment, thereby potentially obviating or lessening the need for an outer frame or an anchoring device, as described below with respect to FIGS. 11-13.

Figure 13:
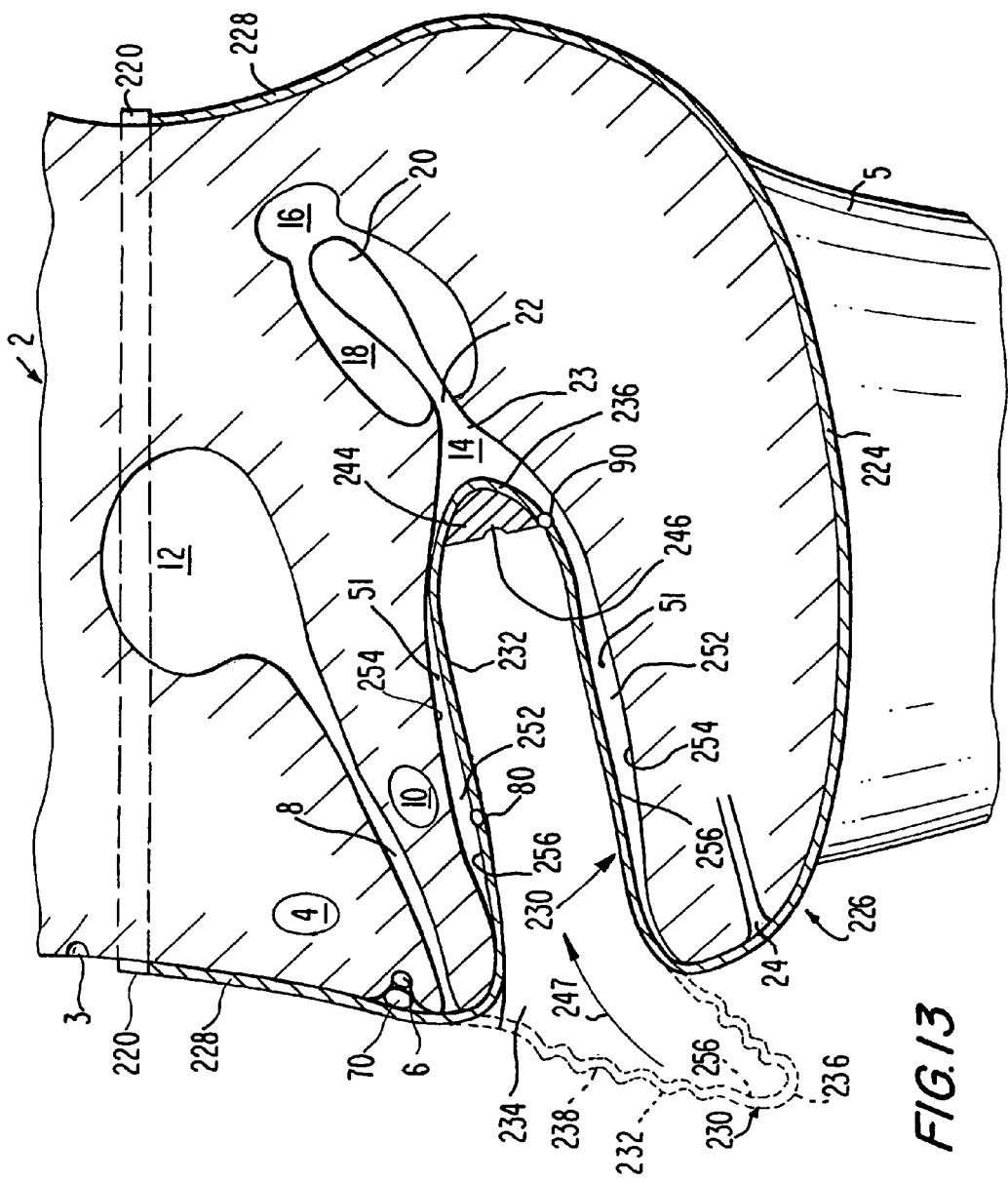
FIG. 13 is a partial cross-sectional view of the female condom of FIGS. 11 and 12, taken from line 13-13 of FIG. 11, illustrating in broken line the pouch portion of the condom in the prior to insertion procedure stage of FIG. 11, and illustrating in solid line the pouch portion of the condom in the insertion procedure stage of FIG. 12.
Figure 14:
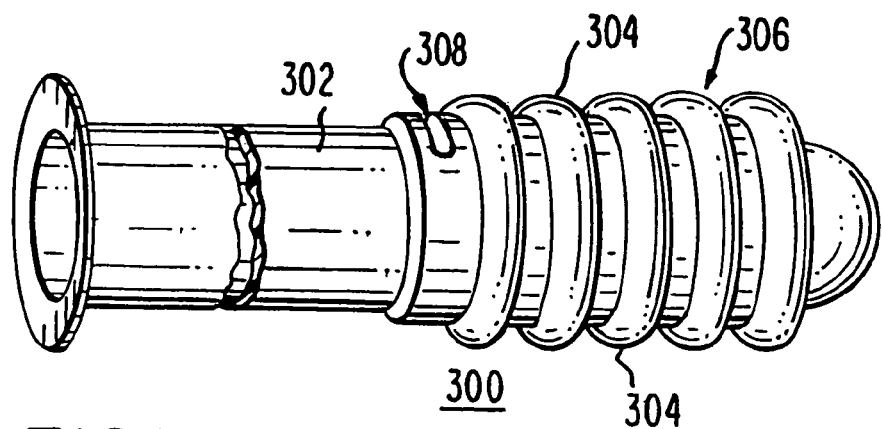
FIG. 14 is a side elevational view of one embodiment of a mold for practicing a method according to the invention.

FIG. 13 illustrates a cross-sectional view of a female pelvic region 2 showing the relative locations of the navel 3, pubic bone 4, leg 5, clitoris 6, urethra 8, G-spot 10, bladder 12, vagina 14, fallopian tube 16, uterus 18, endometrial cavity 20, cervix 22, posterior fornix 23, and rectum 24. A preferred embodiment of a bikini female condom 226 according to the invention is worn about pelvic region 2 of the female in the same manner as any traditional bikini or female undergarment.

Figure 11:
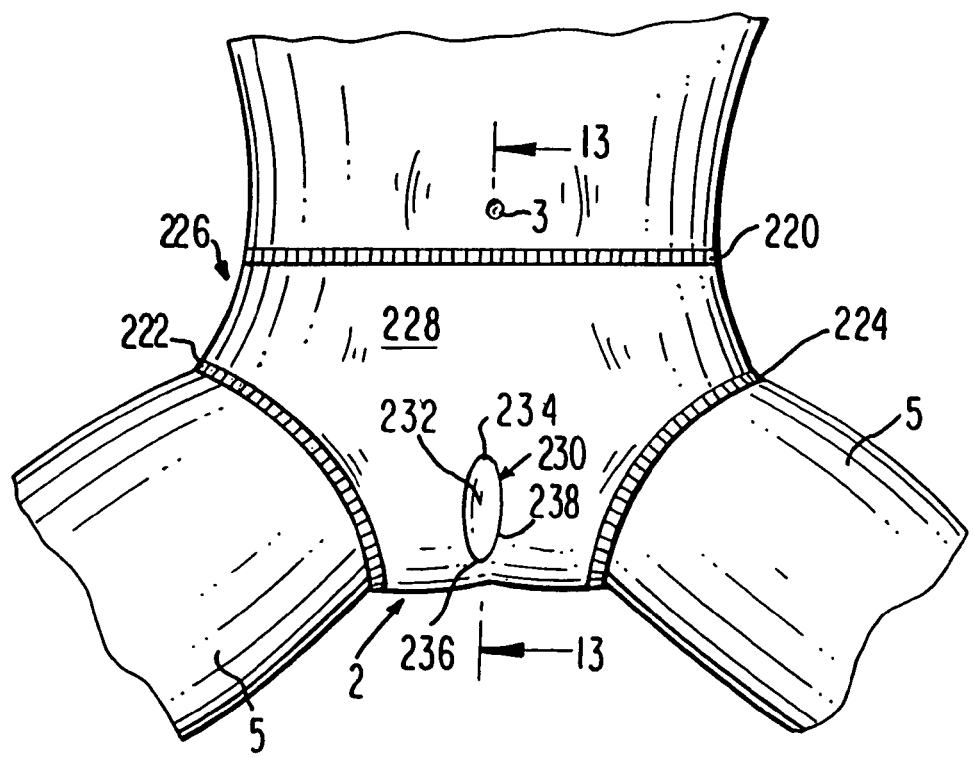
FIG. 11 is a front elevational view of the pelvic region of FIGS. 1 and 3-4C equipped with a second embodiment of a female condom, in a stage prior to an insertion procedure of the condom into the pelvic region, according to the invention.
Figure 12:
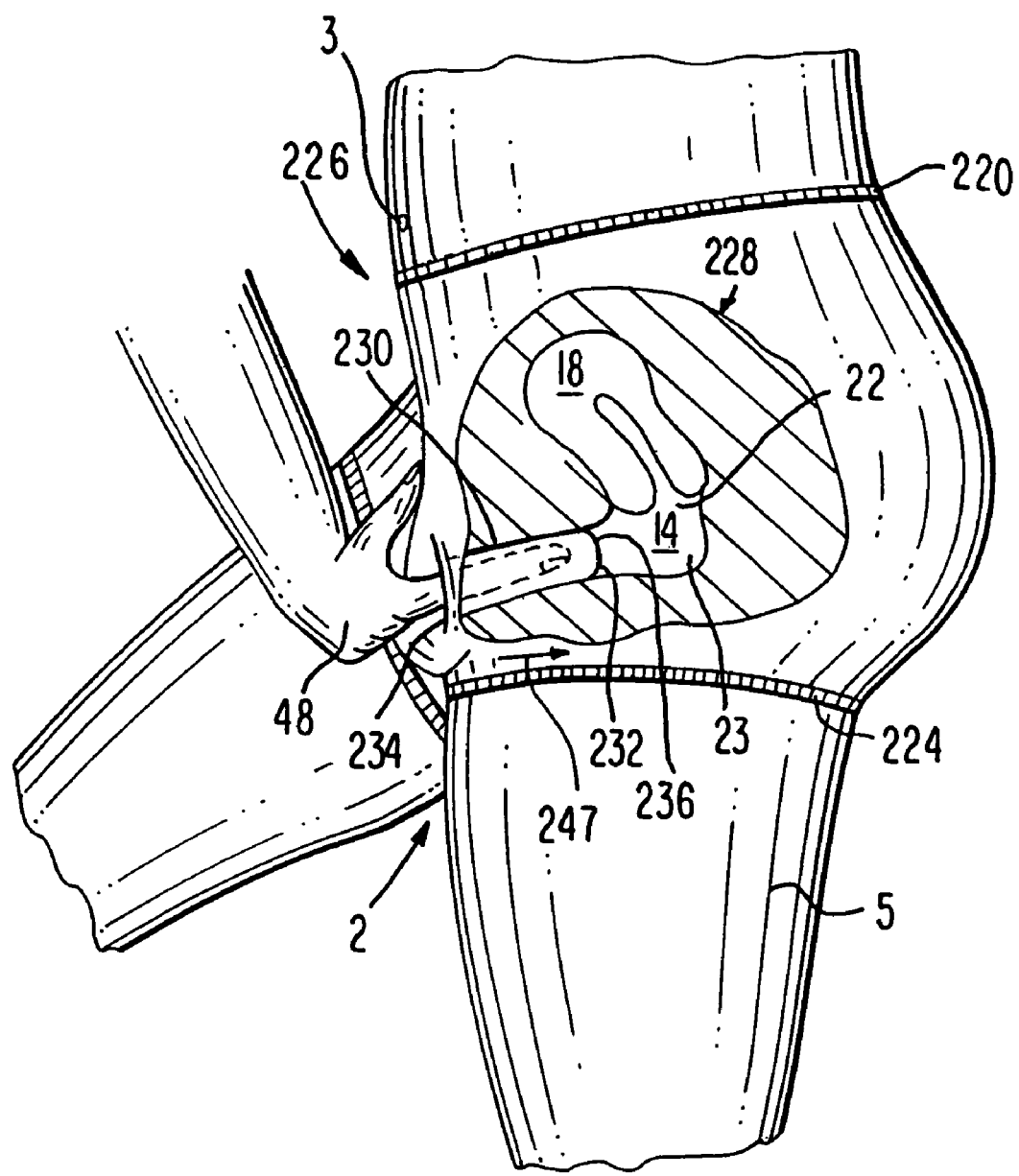
FIG. 12 is a partially sectional perspective view of the female condom of FIG. 11 in a stage of an insertion procedure of the condom into the pelvic region of FIGS. 1, 3-4C, and 11, according to the invention.

As also illustrated in FIGS. 11 and 12, condom 226 includes waist band 220 and upper leg bands 222 and 224, which define the outer boundaries of covering 228 of bikini female condom 226. Bands 220, 222, and 224 may be formed in any desired suitable shape that allows covering 228 of condom 226 to tightly contact the female anatomy about pelvic region 2 such that fluid external to condom 226 may not easily pass into condom 226, and thus not easily pass into vagina 14, when properly worn by the female. Bands 220, 222, and 224 may be formed of any suitable elastic material, such as rubber or latex, that has sufficient flexibility to be easily deformed, but that also is stiff and resilient enough to have a spring bias for maintaining substantially fluid-tight contact with the female anatomy. Covering 228 may be formed of any suitable, substantially fluid tight, material for covering the female anatomy within the boundaries created by bands 220, 222, and 224, such as latex, synthetic latex, polyurethane, thermoplastic elastomers, or neoprene, for example. The bands may be an integral part of the female condom or may be suitable attached about the covering. The bikini female condom may not include bands about the thighs of the user, but may rather be worn like a common swimsuit in the crotch region.

Condom 226 also includes a pouch 230 having an open end 234, a closed end 236, and a resilient tubular body portion 232 that extends longitudinally between open end 234 and closed end 236. Pouch 230 may be integrated by a substantially fluid tight seal at its open end 234 to covering 228 by any suitable process, such as dipping, heat-sealing, stitching, or any other known method.

As described above with respect to tubular portion 32 of FIGS. 1-4C, tubular body portion 232 of pouch 230 may be formed from any suitable elastic membrane material, such as natural latex, polyurethane, thermoplastic elastomers, or any synthetic rubber, such as neoprene, for example. A plurality of bellows-like convolutions or corrugations 238 may preferably be formed along the length of tubular body portion 232 to increase the elasticity of pouch 230, while also providing stimulation to the penis during sexual intercourse and enabling conformance of pouch 230 to the wall of vagina 14. Convolutions 238 are preferably circular and are formed to act in a spring-like manner, whereby if pouch 230 is extended in the longitudinal direction into an elongated configuration, by the insertion of a penis or the like, pouch 230 will return to its original non-extended configuration following withdrawal of the penis due to a spring-like bias in the longitudinal direction, as described above with respect to pouch 30.

Unlike the female condoms described above, bikini female condom 226 preferably does not require an anchor for retaining the closed end of its pouch within vagina 14 of the female user, for reasons described in greater detail below. However, condom 226 may preferably be provided with a cushion 244 within tubular body portion 232 of pouch 230 at closed end 236. Cushion 244 may be any suitable compressible material, as described above with respect to cushion 44 of FIGS. 1-4C, for example. Cushion 244 may be compressed by the tip of a penis during its inward strokes of sexual intercourse, such that upon the following outward strokes of the penis, minimal or no vacuum is created between the tip of the penis and closed end 236 of pouch 230, as described above with respect to cushion 44 (see, e.g., FIGS. 4B and 4C).

A smooth but apertured thin membrane coating made of any suitable material, such as polyurethane or latex, may cover cushion 244 to reduce or prevent any possible abrasion that may result on the penis due to contact with cushion 244. Cushion 244 may also preferably have an insertion indentation 246 formed in the outer surface of cushion 244 facing open end 234 of pouch 230. Insertion indentation 246 is preferably configured to receive a finger of a user to facilitate insertion of condom 226 in vagina 14 so that no separate insertion tool is required (see, e.g., FIGS. 12 and 13). Furthermore, cushion 244 may ensure that a user's finger does not accidentally penetrate closed end 236 of pouch 230 during insertion of condom 226 into vagina 14 or by a penis during sexual intercourse.

Thus, condom 226 may be inserted into vagina 14, and positioned as illustrated in FIG. 12, by inserting one or more fingers 48 through the open end 234 of pouch 230, and into the interior of tubular body portion 232 and by pushing, and preferably by rotating, closed end 236 and cushion 244 into the canal of vagina 14, in the direction of arrow 247, as illustrated in FIGS. 12 and 13. The tip of the at least one finger 48 may push closed end 236 towards cervix 22 at the end of the canal of vagina 14 near posterior fornix 23, such that fluid 51 (e.g., air or any natural female juices) within vagina 14 is expelled from vagina 14, along a passageway 252 between the exterior of tubular body portion 232 and the wall of vagina 14, and preferably from within condom 226, thereby creating at least a partial vacuum between wall 254 of vagina 14 and the exterior wall 256 of tubular body portion 232 to retain closed end 236 of condom 226 within vagina 14, as described in more detail below.

Due to this expulsion of fluid 51 from vagina 14, the pressure within passageway 252 drops and creates at least a partial vacuum therein. This vacuum in combination with the substantially fluid-tight seal between the female anatomy and condom 226 (due to bands 220, 222, and 224) pulls pouch 230 inside vagina 14 in the direction of arrow 247 and pulls covering 228 against the female anatomy external to vagina 14, as shown in FIG. 13, thereby preventing fluid 51 from re-entering vagina 14. Therefore, the vacuum is maintained so as to retain closed end 236 at the end of the canal of vagina 14 near posterior fornix 23.

Lubrication may preferably be provided on exterior wall 256 of tubular body portion 232 to act as an effective sealant with wall 254 of vagina 14, thereby assisting in maintaining the vacuum. As described above with respect to FIGS. 1-4C, any suitable lubrication may be used for this purpose, but the type of lubrication preferably varies depending on the material used to form tubular body portion 232. In a preferred embodiment, one or more stimulating devices (e.g., stimulators 70, 80, and/or 90) may be provided with condom 226, as described above with respect to condom 26.

Once closed end 236 has been retained at the end of the canal of vagina 14, open end 234 of pouch 230 of condom 226 may then receive a penis to initiate sexual intercourse, as similarly described above with respect to pouch 30 of condom 26 (see, e.g., FIGS. 4B and 4C). Like cushion 44 of condom 26, cushion 244 of condom 226 preferably prevents a negative pressure from being created between the tip of a penis and closed end 236 of condom 226 during the outward stroke of the penis, such pressure could overpower the vacuum created by insertion of closed end 236 into vagina 14 and thus loosened closed end 236 from its retained state.

A method of making the female condom of this invention includes the step of providing a mold 300 (see, e.g., FIG. 14) having an elongated cylindrical portion 302 and an outer surface 304 on one end thereof for preferably defining a convolution 306 and a sack 308 thereon, which in turn define a spring formation and a stimulator sack, respectively. Next, the method preferably includes the step of dipping mold 300 into a liquid elastomeric material to form a thin elastic membrane having a first spring action, and forming a pouch (e.g., pouch 30) with an open end (e.g., end 34), a closed end (e.g., end 36), and a tubular body portion (e.g., portion 32) formed and extending longitudinally therebetween. Preferably the membrane formed by the mold also includes a convolution (e.g., convolution 38) shaped in the form of convolution 306 on mold 300 formed integrally of the tubular wall adjacent the closed end that will produce spring movement independently of the elasticity of the elastomeric material.

Consistent with the embodiments of the female condom inventions described above, the method also contemplates the steps of providing a mold having anyone of the following configurations, as described in Alla et al. U.S. Pat. No. 6,000,398, which is hereby incorporated by reference herein in its entirety: a mold that is provided with a convolution having a helically shaped outer surface defining a spring formation; a mold that is provided with a series of circumferentially spaced surface segments that are axially spaced from a second series of circumferentially spaced surface segments to form the spring formation; a mold that is provided with circumferentially spaced surface segments formed as arcuate segments staggered on opposite sides of the circumference of the mold to form the spring formation; a mold that is provided with circumferentially spaced surface segments that are arcuate segments staggered on opposite sides of the circumference of the mold at staggered locations along the length of the mold to form the spring formation; and a mold that is provided with surface convolutions forming a series of sinusoidal shapes formed around the tip of the mold to form the spring formation.

After dipping mold 300 into the liquid elastomeric material to form the thin elastic membrane having a first spring action and a pouch as described above, mold 300 and its thin elastic membrane is then preferably dried, re-dipped, dried, vulcanized, leached in a trisodium phosphate tank, and then wet stripped. The resultant wet pouch of the female condom is then preferably fed into a washing machine and washed for about one hour with a solution containing silicone emulsion and cornstarch or magnesium carbonate, for example. The washed pouch of the female condom is then preferably post-cured in a separate drier. The dried pouch is then tested in its expanded configuration in a conventional dry or wet testing device such that minute pinholes and weak spots are rejected electronically.

Next a frame (e.g., frame 28), preferably made of a medical grade, polyvinyl chloride in a triangular shape, is then attached to the open end of the pouch by a simple roll-on operation such that the thin elastic membrane film of the pouch is preferably rolled at least three times about the frame.

Next, a retention anchor (e.g., anchor 40) cut to the desired shape is attached to the closed end of the pouch and external to the pouch by mechanical or other known means. Then, a cushion (e.g., cushion 44) cut to the desired shape is placed on the end of a mandrel. The pouch is then stretched over the mandrel such that the cushion is locked at the closed end of the pouch and internal to the pouch by mechanical or other known means. The pouch is removed from the mandrel gently such that the cushion remains embedded inside the pouch at its closed end.

If mold 300 was provided with one or more sacks 308, then the sacks (e.g., sack 78) thereby formed in the pouch may have stimulators (e.g., stimulators 700, 800, and/or 900) inserted therein, if such stimulators are to be packaged with the female condom. If mold 300 was not provided with sacks 308, then one or more stimulators may be mechanically fixed, adhered, or coupled by any other known means to the pouch, if such stimulators are to be packaged with the female condom. In alternative embodiments, various stimulators may be separately provided to a user for use with the female condoms of the invention.

Finally, according to a preferred method of the invention, the female condom is then packed into a preferably rectangular, laminated aluminum foil packaging container. Lubrication, for example 0.5 cubic centiliters of silicon oil lubricant, may preferably be dripped onto each side (i.e., the interior and exterior of the tubular body portion) of the pouch just prior to sealing the packaging container.

Figure 15:
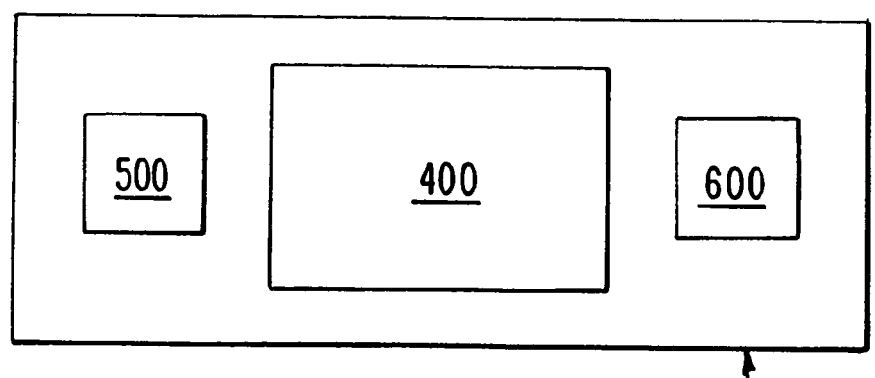
FIG. 15 is a simplified block diagram of an illustrative kit incorporating a female condom, according to the invention.

FIG. 15 illustrates a female condom 400 of the invention provided in a package or kit 1000. Kit 1000 may include one or more type of fluid 500 and one or more set of instructions 600. Fluid 500 may include any lubrication, as described above with respect to FIGS. 1-4C, and any other fluid that may maintain the functionality and sterility of condom 400 if it is not used for a certain amount of time after manufacture, for example. Instructions 600 may be any written and/or graphical information that teaches a user how to properly access and use the female condom 400. Kit 1000 may be a container, such as a sealed bag or laminated aluminum foil, that maintains the relationship between its contents before the use thereof by a user.

Thus, it is seen that a female condom with a pouch and an anchor for retaining the pouch within a vagina during sexual intercourse has been provided. It should be noted that the shapes and sizes of the pouches, anchors, frames, and stimulators described above are only exemplary. One skilled in the art will appreciate that the invention can be practiced by other than the described embodiments, which are presented for purposes of illustration and not of limitation, and the invention is limited only by the claims which follow.

What is claimed is:

1. A female condom, said condom comprising:
a pouch having an open end, a closed end, and a tubular body extending longitudinally between said open end and said closed end, wherein said tubular body has a wall with an interior and an exterior;
a joiner portion coupled to and extending from said closed end of said pouch; and
an anchor coupled to said joiner portion outside of said pouch and extending longitudinally away from said tubular body at said closed end, wherein said anchor is capable of forming at least a partial vacuum between a wall of a vagina into which the condom is inserted and said exterior of said tubular body.

2. The condom of claim 1, wherein said anchor is compressed so as to form said vacuum during the insertion of said condom in the vagina.

3. The condom of claim 2, wherein said compression of said anchor expels fluid from within said anchor to outside the vagina.

4. The condom of claim 1 further comprising:
a frame having an orifice therethrough, wherein said open end of said pouch is attached to said frame about said orifice.

5. The condom of claim 4, wherein said orifice and said open end of said pouch provide a passageway into said interior of said tubular body.

6. The condom of claim 4, wherein said vacuum pulls said frame towards said anchor when the condom is inserted into the vagina.

7. The condom of claim 4, wherein said frame further comprises a pocket that aligns with the clitoris of the female when said frame contacts the female anatomy external to the vagina on insertion of the condom into the vagina and during sexual intercourse.

8. The condom of claim 7, wherein said frame further comprises a stimulating device within said pocket.

9. The condom of claim 8, wherein said stimulating device is a vibrator.

10. The condom of claim 8, wherein said stimulating device includes a set of movable rings.

11. The condom of claim 8, wherein said stimulating device includes a sleeve mounted on a rotor.

12. The condom of claim 8, wherein said stimulating device includes an offset rotor shaft.

13. The condom of claim 1, wherein said pouch further comprises a stimulating device coupled to said tubular body.

14. The condom of claim 1, wherein said pouch further comprises a stimulating device coupled to said closed end.

15. The condom of claim 1, wherein said anchor is a sponge.

16. The condom of claim 1, wherein said anchor is a cup.

17. The condom of claim 1, wherein said tubular body is elastic.

18. The condom of claim 1, wherein said tubular body has a longitudinal length that is equal to or shorter than the longitudinal length of the vaginal canal.

19. The condom of claim 1, wherein said wall of said tubular body is straight as it extends longitudinally between said open end and said closed end.

20. The condom of claim 1, wherein said wall of said tubular body is bellowed as it extends longitudinally between said open end and said closed end.

21. The condom of claim 1, wherein said exterior of said tubular body is lubricated.

22. The condom of claim 1 further comprising:
a cushion attached to the inside of said closed end of said tubular body.

23. The condom of claim 22, wherein said cushion further comprises an indentation for receiving a user's finger to facilitate insertion of said condom in the vagina.

24. The condom of claim 22, wherein said cushion is compressed by the inward stroke of a penis during sexual intercourse.

25. A kit including said condom of claim 1 and instructions on use of said condom.

26. The kit of claim 25, wherein said kit contains said condom in a sterile environment.

27. The kit of claim 25, wherein said kit contains lubricant.

* * * * *